(12) United States Patent
Batzer

(10) Patent No.: US 12,714,344 B2
(45) Date of Patent: Aug. 25, 2026

(54) INTEGRATED DIFFERENTIAL VOLTAGE MEASURING SYSTEM

(71) Applicant: Siemens Healthcare GmbH, Erlangen (DE)

(72) Inventor: Ulrich Batzer, Spardorf (DE)

(73) Assignee: Siemens Healthineers AG, Forchheim (DE)

( * ) Notice: Subject to any disclaimer, the term of this patent is extended or adjusted under 35 U.S.C. 154(b) by 582 days.

(21) Appl. No.: 17/850,612

(22) Filed: Jun. 27, 2022

(65) Prior Publication Data

US 2023/0000413 A1 Jan. 5, 2023

(30) Foreign Application Priority Data

Jun. 30, 2021 (DE) .................... 10 2021 206 864.2

(51) Int. Cl.
*A61B 5/263* (2021.01)

(52) U.S. Cl.
CPC ...... *A61B 5/263* (2021.01); *A61B 2562/0209* (2013.01)

(58) Field of Classification Search
CPC ... A61B 5/263; A61B 2562/0209; A61B 5/28; A61B 5/277; A61B 5/369; A61B 5/389
See application file for complete search history.

(56) References Cited

U.S. PATENT DOCUMENTS

2005/0177038 A1* 8/2005 Kolpin .................. A61B 5/302 600/372
2010/0036230 A1 2/2010 Burnham et al.
2012/0116198 A1* 5/2012 Veen .................... A61B 5/7214 600/372
2013/0204110 A1 8/2013 Ko et al.
2013/0211208 A1* 8/2013 Varadan ............... A61B 5/6804 600/300
2014/0213882 A1* 7/2014 Chung ................ A61B 5/0006 600/372

(Continued)

FOREIGN PATENT DOCUMENTS

CN 202699127 U 1/2013
CN 103239221 A 8/2013

(Continued)

OTHER PUBLICATIONS

Mearthane Products Corporate. Polyurethane Volume Resistivity. https://knowledgecenter.mearthane.com/polyurethanevolumeresistivity (Year: 2018).*

(Continued)

*Primary Examiner* — Linda C Dvorak
*Assistant Examiner* — William Mossbrook
(74) *Attorney, Agent, or Firm* — Harness, Dickey & Pierce, P.L.C.

(57) ABSTRACT

An integrated differential voltage measuring system for measuring bioelectrical signals of a patient, includes at least two signal measuring circuits, each of the at least two signal measuring circuits including a sensor electrode; a reference measuring circuit comprising a reference electrode; and a shared electrically conductive electrode covering, wherein the electrically conductive electrode covering superimposes at least a region that is formed by the base areas of the sensor electrodes and reference electrode.

19 Claims, 3 Drawing Sheets

(56) References Cited

U.S. PATENT DOCUMENTS

| | | | | |
|---|---|---|---|---|
| 2017/0303810 | A1* | 10/2017 | Stone | A61B 5/6893 |
| 2018/0146923 | A1 | 5/2018 | Fridman et al. | |
| 2019/0200889 | A1* | 7/2019 | Stone | A61B 5/6823 |
| 2020/0046964 | A1 | 2/2020 | Rotman et al. | |
| 2020/0297282 | A1 | 9/2020 | Batzer | |

FOREIGN PATENT DOCUMENTS

| | | | | |
|---|---|---|---|---|
| CN | 209315868 | U | 8/2019 | |
| CN | 110811605 | A | 2/2020 | |
| DE | 102019203627 | A1 | 9/2020 | |
| GB | 2353594 | A | 2/2001 | |
| KR | 20190038233 | A | 4/2019 | |
| WO | WO-02065905 | A1 * | 8/2002 | A61B 5/6831 |
| WO | WO-2008152588 | A2 * | 12/2008 | A61B 5/30 |
| WO | WO-2011084450 | A1 * | 7/2011 | A61B 17/06166 |

OTHER PUBLICATIONS

Laminated Plastics. Technical Data Sheet Nylon. https://laminatedplastics.com/nylon.pdf (Year: 2017).*

Helmenstine, Anne. Table of Electrical Resistivity and Conductivity. https://www.thoughtco.com/table-of-electrical-resistivity-conductivity-608499 (Year: 2024).*

* cited by examiner 33
34
35
30
28
36
S
25
27
27a
27b
6a
26
31
ES
E
22
C
P
3a
3
4
6
5
1a
30

INTEGRATED DIFFERENTIAL VOLTAGE MEASURING SYSTEM

CROSS-REFERENCE TO RELATED APPLICATION(S)

The present application claims priority under 35 U.S.C. § 119 to German Patent Application No. DE 102021206864.2, filed Jun. 30, 2021, the entire contents of which are incorporated herein by reference.

FIELD

Some example embodiments of the present invention relate to an integrated differential voltage measuring system for measuring bioelectrical signals of a patient, comprising an electrode covering which is in particular electrically conductive.

BACKGROUND

Voltage measuring systems, in particular differential voltage measuring systems, for measuring bioelectrical signals are used in the field of medicine, for example, to measure electrocardiograms (ECG), electroencephalograms (EEG) or electromyograms (EMG).

The measurement of cardiac activity using the cited voltage measuring systems is required for imaging of the heart in particular, in order to adapt the imaging operation to the highly distinctive movement of the heart during the heartbeat. To this end, use is conventionally made of sensors which have to be fastened to the body of the patient. One possibility for measuring the heartbeat is a capacitive ECG, in which an ECG signal is picked up in a purely capacitive manner and without any direct contact between patient and sensor, in particular through clothing of the patient. In order to achieve a good signal quality of the heartbeat signal, the measured signal must preferably have a high amplitude. This can be achieved by means of a high capacitance between patient and sensor. The capacitance can be directly influenced by the size of the coupling area between sensor and patient. The greater the coupling area, the greater the capacitance that is achieved.

SUMMARY

In order to suppress interference in measured signals, provision is customarily made for protective measures in the form of a e.g. a ground connection of the voltage measuring system or a reference electrode (neutral driven electrode: NDE). These are often provided at least partially as sensor elements which are separate from the sensor electrodes that capture the measured signals. This increases the preparation effort involved in a capacitive ECG measurement, since the various sensor elements have to be arranged or held in a desired position at the patient.

In addition to this, use is customarily made of capacitive ECG arrangements which are integrated in a layered manner in conductive textiles, the conductivity being achieved by means of a vapor deposition process using conductive particles, for example. The reference electrode is often embodied as a separate sensor element in this case. The use of textiles in a sensor element also makes the cleaning process more difficult. Moreover, textiles are not transparent to x-rays and are therefore not suitable for triggering all types of medical image data capture.

According to at least one example embodiment, an integrated differential voltage measuring system for measuring bioelectrical signals of a patient, the integrated differential voltage measuring system including at least two signal measuring circuits, each of the at least two signal measuring circuits including a sensor electrode; a reference measuring circuit comprising a reference electrode; and a shared electrically conductive electrode covering, wherein the electrically conductive electrode covering superimposes at least a region that is formed by the base areas of the sensor electrodes and reference electrode.

According to at least one example embodiment, the sensor electrodes and the reference electrode have a layer-type structure, each of the sensor electrodes and the reference electrode including at least one upper electrically conductive layer.

According to at least one example embodiment, the electrically conductive electrode covering has a layer thickness of less than 100 μm.

According to at least one example embodiment, the electrically conductive electrode covering is made from a synthetic material.

According to at least one example embodiment, the electrically conductive electrode covering is enriched with carbon particles.

According to at least one example embodiment, the electrically conductive electrode covering has a surface resistance which is greater than 500 MOhm.

According to at least one example embodiment, the electrically conductive electrode covering has a bulk resistance of less than 100 MOhm.

According to at least one example embodiment, the electrically conductive electrode covering is made from a hygroscopic material.

According to at least one example embodiment, the base area of the reference electrode corresponds to a multiple of the base area of one of the sensor electrodes.

According to at least one example embodiment, the reference electrode surrounds each sensor electrode over an angular range of at least 180°.

According to at least one example embodiment, an impedance between the reference electrode and each sensor electrode is greater than 100 MOhm in each case.

According to at least one example embodiment, the differential voltage measuring system further includes a grounding circuit including a grounding electrode, a base area of the grounding electrode is superimposed by the electrically conductive electrode covering.

According to at least one example embodiment, an impedance between grounding electrode and each sensor electrode is greater than 1 GOhm, and an impedance between the grounding electrode and the reference electrode is greater than 200 MOhm.

BRIEF DESCRIPTION OF THE DRAWINGS

The present invention is explained again in greater detail below with reference to the appended figures and on the basis of exemplary embodiments. Identical components in the various figures are denoted by identical reference numerals. The figures are not generally to scale.

DETAILED DESCRIPTION

Figure 1:
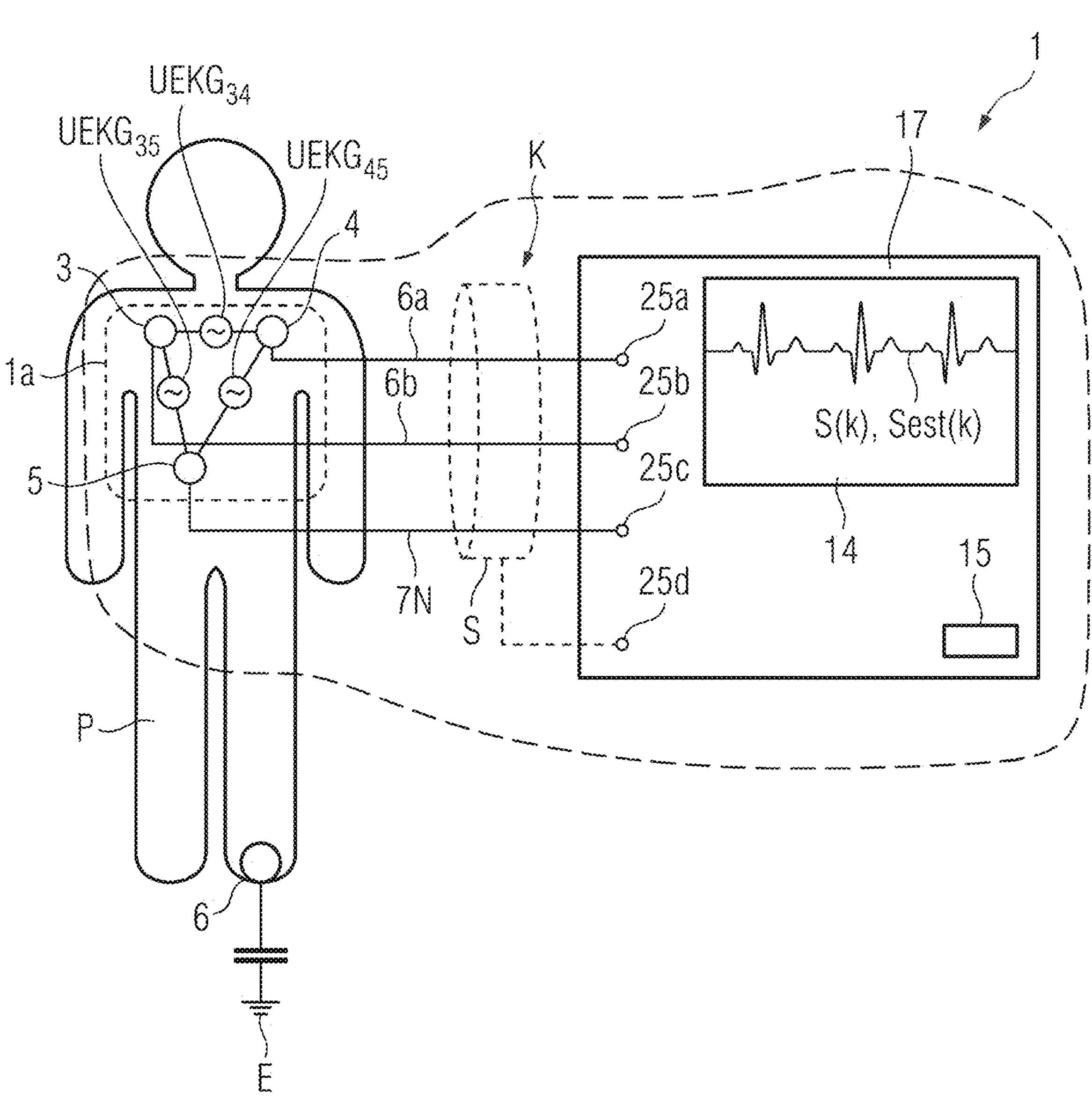
FIG. 1 shows a view of a differential voltage measuring system which is arranged against a patient in an exemplary embodiment.

Example embodiments of the present invention provide means which ensure reliable suppression of interference at the same time as simple operation, and which satisfy the hygiene requirements of a clinical environment in respect of impermeability to water and ease of cleaning.

This is achieved at least by a differential voltage measuring system according to the independent claim 1. Further particularly advantageous embodiments and developments of the present invention are specified in the dependent claims and in the following description, wherein individual features of different exemplary embodiments or variants can also be combined to form further exemplary embodiments or variants.

Example embodiments of the present invention relate to an integrated differential voltage measuring system for measuring bioelectrical signals of a patient. The inventive differential voltage measuring system captures bioelectrical signals from e.g. a human or animal patient. For this purpose, it has a number of measuring lines or useful-signal paths. In the form of individual cables, for example, these connect electrodes that are placed on the patient for the purpose of capturing signals to further components of the voltage measuring system, i.e. in particular to an electronics module which is used to evaluate and/or represent the captured bioelectrical signals, in particular heartbeat signals.

The differential voltage measuring system can be designed in particular as an electrocardiogram (ECG), electroencephalogram (EEG) or electromyogram (EMG).

The differential voltage measuring system has at least two signal measuring circuits, each corresponding to a useful-signal path and each comprising a sensor electrode. The voltage measuring system can comprise precisely two but also more than two signal measuring circuits.

The signal measuring circuits each have, in addition to the sensor electrode, a measuring amplifier circuit and a sensor line between the measuring amplifier circuit and the sensor electrode. In embodiments of the present invention, the sensor lines are used to transfer the bioelectrical measured signals captured by the sensor electrode to the respective measuring amplifier circuit. The measuring amplifier circuit preferably comprises an operational amplifier, which can be designed as a back-coupled device. This means that the negative input of the operational amplifier, also referred to as an inverting input, is coupled to the output of the operational amplifier, thereby generating a high virtual input impedance at the positive input.

The voltage measuring system further comprises a reference measuring circuit comprising a reference electrode. The reference electrode and the associated reference measuring circuit are used to achieve a potential equalization between the patient and the ECG measuring device. In embodiments of the present invention, the reference measuring circuit likewise comprises a signal line and an operational amplifier.

The sensor electrodes and the reference electrode are each designed as planar electrodes and have a film-type structure. In other words, they are significantly smaller in one spatial dimension than in the two other spatial dimensions. The electrodes can have any desired shape. In particular, the sensor electrodes can have a base area which is round, rectangular or e.g. elliptical. The sensor electrodes and the reference electrode can be composed of the following materials or comprise at least one of said materials: metallic sheets or films, textiles which are rendered conductive by means of vapor deposition or by other methods, or other conductive materials such as carbon or materials with carbon admixture.

The sensor electrodes and the reference electrode are constructed in a layered manner in particular. Both forms of electrode have at least one electrically conductive layer. The conductive layers preferably have a maximum surface resistance of 100 kOhm. The conductive layer is oriented towards the electrode covering and/or in the direction of the patient.

In embodiments, any of the sensor electrodes can comprise further layers, e.g. for the purpose of passive shielding of strong electromagnetic interference, or for active shielding by providing a high input impedance. The reference electrode can likewise comprise further shielding layers. All further layers are arranged on that side of the electrically conductive layer which faces away from the patient.

The sensor electrodes and the reference electrode are inventively arranged adjacent to or interposed with each other, extending on the same plane. They have a defined distance from each other. In this case, the reference electrode is so designed as to surround the sensor electrodes at least partially.

The sensor electrodes have a respective diameter or side length in the range from 3 cm to 6 cm, preferably 4 cm to 5 cm, in the case of a circular or rectangular embodiment. In preferred embodiments of the present invention, the sensor electrodes have the same basic shape, but can also have different shapes.

The reference electrode has a diameter or maximum side length in the range between 15 cm and 30 cm, preferably between 18 cm and 25 cm.

The sensor line of a signal measuring circuit is used to transfer the measured signals captured by means of the sensor electrode to the measuring amplifier. The measuring amplifier circuit preferably comprises an operational amplifier, which can be designed as a back-coupled device. This means that the negative input of the operational amplifier, also referred to as an inverting input, is coupled to the output of the operational amplifier, thereby generating a high virtual input impedance at the positive input.

Sensor lines and signal line and further components of the signal measuring circuits and reference measuring circuit are inventively arranged outside the plane of the electrodes, preferably on that side of the electrode plane which faces away from the patient.

The inventive voltage measuring system is further characterized by a shared electrically conductive electrode covering, which superimposes at least a region that is formed by the base areas of the sensor electrodes and the reference electrode. The electrically conductive electrode covering is designed as a unitary part.

In other words, the shared electrode covering superimposes both the two sensor electrodes and the reference electrode. In embodiments, the electrode covering extends beyond the area that is formed by the base areas of sensor electrodes and reference electrode, and is itself therefore larger. In preferred embodiments of the present invention, the electrode covering has a diameter or a side length respectively in the range from 15 cm to 30 cm, preferably between 20 cm and 35 cm.

According to example embodiments of the present invention, the sensor electrodes, the reference electrode and the electrically conductive electrode covering or the inventive voltage measuring system are designed as an integral sensor element which is positioned against or on the patient for the purpose of an ECG measurement and is used for both the ECG signal capture and potential equalization.

It is thereby possible to reduce the preparation effort involved in an ECG measurement since only one sensor element or fewer sensor elements have to be positioned against the patient.

Example embodiments of the present invention is based on the finding that in particular textiles with cotton content have a bulk resistance between 100 MOhm and 1000 MOhm in a dry state. Practice shows that following humidification by means of spray mist or sweat of the patient, the bulk resistance during an ECG measurement in the case of cotton and many other textiles typically falls below 10 MOhm, sometimes even to below 1 MOhm.

A structure comprising a purely capacitive ECG with the electrodes embedded in textile layers is therefore not considered to be suitable, since an ohmic connection would be suppressed in this case.

According to example embodiments of the present invention, a differential voltage measuring system functions both with ohmically insulating layers and at the same time, using ohmically conductive layers, exploits the advantages of this electrical conductivity. The inventive differential voltage measuring system is therefore so designed as to also provide an ohmically conductive connection. The differential voltage measuring system is designed in a particularly advantageous manner to have a maximum bulk resistance of 10 MOhm in the dry state and a maximum bulk resistance of 1 MOhm when humidity is added.

This and all of the following resistance details comply with the requirements of DIN EN 61340-2-3 (VDE 0300-2-3), Elektrostatik—Teil 2-3: Prüfverfahren zur Bestimmung des Widerstandes and des spezifischen Widerstandes von festen Werkstoffen, die zur Vermeidung elektrostatischer Aufladung verwendet werden [Electrostatics—Part 2-3: Test methods for the determination of the electrical resistance and resistivity of solid materials used to avoid electrostatic charge accumulation] (IEC 61340-2-3: 2016).

In a particularly advantageous manner, the present invention uses the electrical conductivity for both the sensor electrodes and for the interference suppression by means of a reference electrode.

The conductive design of the electrode covering, the sensor electrodes and the further electrodes means that, in addition to the capacitive coupling for capacitive measurement of an ECG signal, under suitable environmental conditions, an ohmic connection can develop between patient and electrodes. In this configuration, capacitive resistance and ohmic resistance are connected in parallel.

In embodiments of the differential voltage measuring system, the electrically conductive electrode covering has a layer thickness of less than 100 μm, preferably 50 μm. The thinner the electrode covering, the easier it is to shape and also to achieve a particularly low sensor element structure. Thicker embodiment variants are however also possible, e.g. in the range of a few millimeters.

In embodiments of the differential voltage measuring system, the electrically conductive electrode covering is composed of a synthetic material, e.g. a polyamide (PA), polyethylene (PE), polypropylene (PP), polyurethane (PU), polyolefin or polyvinyl chloride (PVC), from which it is particularly easy to manufacture and process the thin layers/films described above. In addition, in comparison with textiles, synthetic materials have particularly good cleaning properties due to their smooth, washable and disinfectable surface.

In order to achieve a desired electrical conductivity of the electrode covering, provision is made in embodiments of the differential voltage measuring system for the electrode covering or the material forming the electrode covering to be enriched with carbon particles. The particles can preferably be nanoparticles. The saturation level of the carbon admixture depends in this case on the desired conductivity and on the type of carbon particles. When selecting the carbon particles, it must be taken into particular consideration that a higher saturation level has a greater effect on the mechanical material properties. In particular, adequate conductivity can already be achieved with a very low saturation level of a few percent by volume as a result of using carbon nanotubes (CNT).

In further embodiments of the differential voltage measuring system, the electrically conductive electrode covering is made from a hygroscopic material. In addition to certain synthetic materials, textiles such as e.g. cotton also have this property. Hygroscopic materials are characterized by a capacity to absorb and store water. They are capable of binding humidity, thereby allowing humidity-dependent adaptation of the electrical conductivity or in particular bulk resistance. The electrode covering is preferably designed to reduce the bulk resistance below 1 MOhm by introducing liquid, e.g. sweat or water. This value corresponds to an electrical conductivity that is achieved by ECG devices with an ohmic connection using textiles that comprise cotton or a less conductive base material with conductive additives. It is thus possible by means of the differential voltage measuring system to obtain a high-quality ECG signal by means of an ohmic connection.

In particularly preferred embodiments, the conductive electrode covering is made from a hygroscopic synthetic material. This combines the adaptability of the conductivity with the resilience and the effective processing properties of the synthetic materials.

In embodiments of the present invention, the electrically conductive electrode covering is so designed as to have a surface resistance greater than 500 MOhm and a bulk resistance of less than 100 MOhm. These values for the surface resistance and the bulk resistance are advantageous limit values, in order to achieve the advantages of the ohmic connection as described above by virtue of the low bulk resistance and, by virtue of the high surface resistance, to avoid unwanted enlargement of the sensor area and contact with other elements. The resistance values relate to dry environmental conditions without any humidity entering the material of the electrode covering.

In embodiments of the present invention, the base area size of the reference electrode is a multiple of the base area size of a sensor electrode. The base area of the reference electrode can therefore be two times or many times the size of the base area of a sensor electrode. It preferably covers the region between the sensor electrodes completely (or essentially completely/extensively), in order to produce a high capacitance at the same time as a low ohmic resistance when the sensor element that is formed by the differential voltage measuring system is positioned against the patient, who is then covered extensively by the various electrodes.

In order to keep the overall size of the inventive differential voltage measuring system within limits, in embodiments of the present invention, the reference electrode is so shaped as to surround the sensor electrodes over an angular range of at least 180° in each case. With a rectangular design of the sensor electrodes, this means that the reference electrode surrounds the sensor electrode on at least two adjacent sides. The reference electrode can therefore extend at least partially between, alongside or beyond the sensor electrodes. Therefore the regions between the sensor electrodes are advantageously used for the potential equalization that is obtained by means of the reference electrode.

In embodiments, the reference electrode also has a distance from each of the sensor electrodes such that the impedance between reference electrode and sensor electrode is greater than 100 MOhm in each case. This impedance value is achieved at a distance between 0.5 cm and 1.5 cm, in particular 1 cm.

In a particularly advantageous embodiment of the present invention, the differential voltage measuring system also comprises a grounding circuit comprising a grounding electrode, whose base area is superimposed by the electrically conductive electrode covering. This arrangement corresponds to a further degree of integration for the differential voltage measuring system, in which the grounding circuit is now also integrated, again making use of the positive effects of the conductive electrode covering for this purpose.

The grounding electrode is likewise designed as a planar electrode having a layer-type or film-type structure and is likewise arranged on the same plane as the sensor electrodes and reference electrode. The grounding electrode is likewise advantageously sized and is arranged in a space-saving manner between, alongside or beyond sensor electrodes and/or the reference electrode and/or surrounds these at least partially. The grounding electrode also has an electrically conductive layer which is oriented towards the patient and a maximum surface resistance of 100 kOhm. Further shielding layers can be provided on that side which faces away from the patient.

The differential voltage measuring system is intended to be designed in such a way that an impedance value of at least 1 GOhm, preferably at least 10 GOhm, is achieved between grounding electrode and each of the sensor electrodes. This impedance value is achieved by selecting the distance between grounding electrode and each sensor electrode between 1.5 cm and 2.5 cm, preferably 2 cm.

Requirements are fundamentally stricter for the distance between grounding electrode and sensor electrode than between reference electrode and sensor electrode. In the case of lower impedance values, the danger would arise that electrical interference in the measured ECG signal would be increased further by the grounding electrode. In cases where only low electrical interference is to be expected, and where standards allow, it is also possible to reduce the impedance by decreasing the distance.

The differential voltage measuring system is further intended to be designed in such a way that an impedance value of at least 200 MOhm, preferably at least 2 GOhm, is achieved between grounding electrode and reference electrode. This impedance value is achieved by selecting the distance between grounding electrode and reference electrode between 0.5 cm and 1.5 cm, preferably 1 cm.

In the figures, an ECG measuring system 1 is used in each case as an exemplary differential voltage measuring system 1, in order to measure bioelectrical signals S(k), namely ECG signals S(k) in this case. However, the present invention is not restricted thereby.

FIG. 1 shows a view of a differential voltage measuring system 1 in the form of an ECG measuring system 1 which is arranged against a patient P in an exemplary embodiment. The voltage measuring system 1 comprises an ECG device 17 with its electrical connection points, and electrodes 3, 4, 5 which are connected thereto via cables K in order to measure ECG signals S(k) at the patient P.

In order to measure the ECG signals S(k), at least a first sensor electrode 3 and a second sensor electrode 4 are required, these being placed against, on top of or underneath the patient P. By means of signal measuring cables K, the electrodes 3, 4 are attached to the ECG device 17 via connection points 25*a*, 25*b*, which are usually plug-type connections. In this case, the first electrode 3 and the second electrode 4 together with the signal measuring cables K form part of a signal capture unit by means of which the ECG signals S(k) can be captured.

A third electrode 5 serves as a reference electrode, in order to ensure potential equalization between the patient P and the ECG device 17. This third electrode 5 is conventionally attached to the right-hand leg of the patient P (right-leg drive: RLD) via a separate sensor element. Here it is however an integral part of a sensor element 1*a*, i.e. developed together with the sensor electrodes 3 and 4 as explained in greater detail with reference to the further figures. Moreover, a multiplicity of further contacts for further derivations (potential measurements) can be attached to the patient P via further connection points (not shown) at the ECG device 17, and used for the generation of suitable signals. The sensor element 1*a* can also have further sensor electrodes (not shown).

Voltage potentials UEKG34, UEKG45 and UEKG35 are generated between the individual electrodes 3, 4, 5 and used to measure the ECG signals S(k).

The directly measured ECG signals S (k) are displayed on a user interface 14 of the ECG device 17.

During the ECG measurement, the patient P is coupled at least capacitively (represented by a coupling on the right leg) to the ground potential E via the grounding circuit, which comprises a grounding electrode 6 and is likewise designed as a separate sensor element here. Alternatively or in parallel, the separate sensor element can also provide an ohmic coupling if configured correspondingly.

In alternative embodiments, as shown with reference to the further figures, the grounding electrode can also be designed as an integral part of the sensor element 1*a*.

The signal measuring cables K which lead from the first sensor electrode 3 and the second sensor electrode 4 to the ECG device 17 are part of the useful-signal paths 6*a*, 6*b*. The signal measuring cable K which leads from the reference electrode 5 to the ECG device 17 corresponds here to part of a third useful-signal path 7N. The third useful-signal path 7N transfers interference signals that were coupled in via the patient P and the electrodes.

The cables K have a shield S which is illustrated schematically here as a broken-line cylinder surrounding all the useful-signal paths 6*a*, 6*b*, 7N. The shield does not actually have to surround all the cables K together, as the cables K can also be shielded separately. However, each connection point 25*a*, 25*b*, 25*c* preferably has an integrated terminal for the shield S. These terminals are then consolidated at a shared shield-connection point 25*d*. In this case, the shield S is designed as e.g. a metal film which surrounds the conductor of the respective cable K but is insulated from the conductor.

As shown in FIG. 1, the ECG device 17 can also have an external interface 15 in order to provide e.g. a connection point for a printer, a storage device and/or even a network. The ECG device 17 also has, assigned to the respective connection points 25*a*, 25*b*, signal measuring circuits 30 (see e.g. FIG. 2) according to exemplary embodiments of the present invention.

Figure 2:
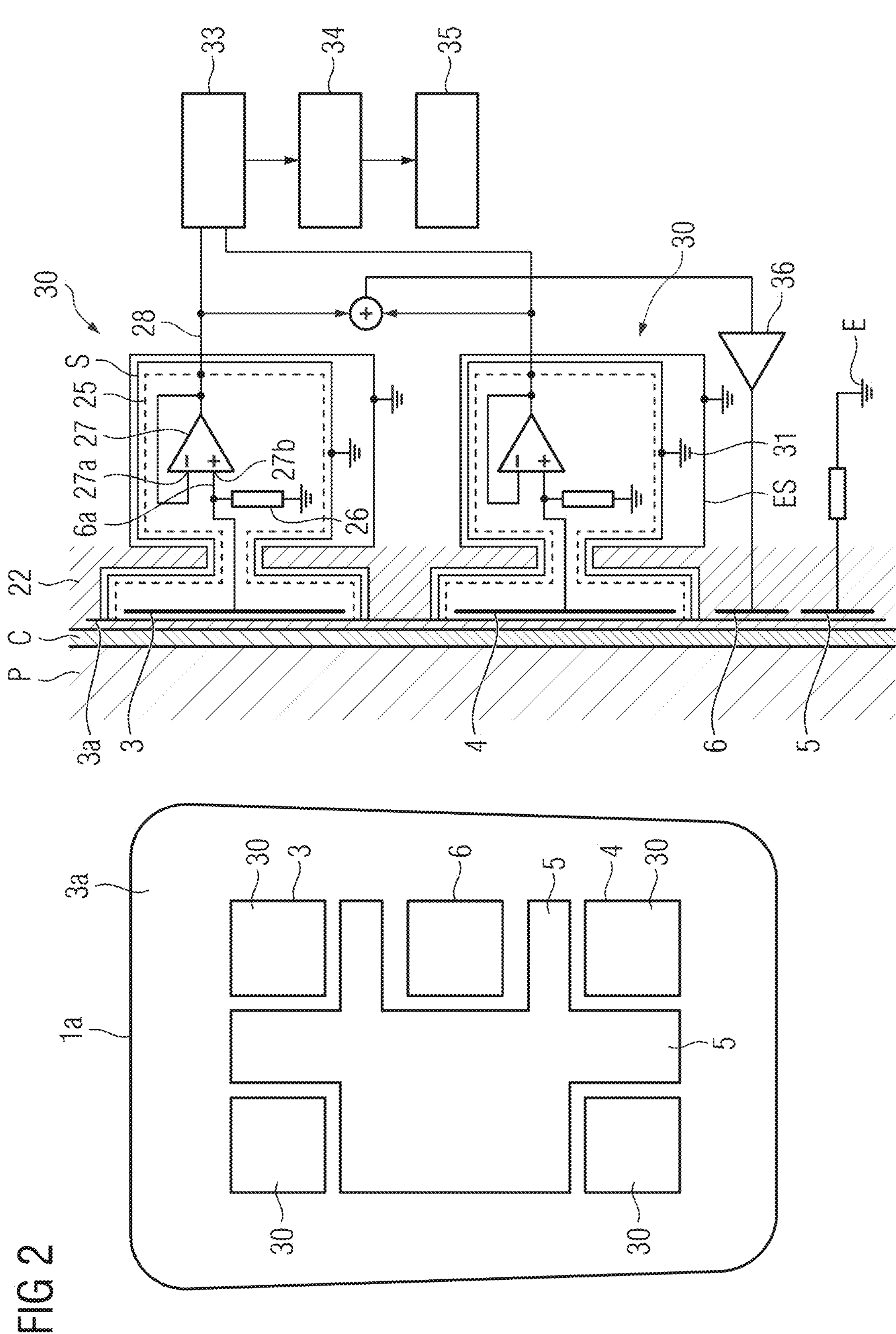
FIG. 2 shows a view of a differential voltage measuring system in another exemplary embodiment.

FIG. 2 shows a view of a differential voltage measuring system 1 in a further exemplary embodiment of the present invention, comprising four signal measuring circuits 30 in an exemplary embodiment. The four signal measuring circuits 30 have an identical structure and therefore, for the sake of clarity, corresponding components of the signal measuring circuits 30 are generally denoted by reference signs only once.

The arrangement of an individual sensor electrode 3, 4 is illustrated here in the form of a fundamentally capacitive ECG measuring circuit. Patient P and sensor electrodes 3, 4 are in close physical proximity to each other. More precisely stated, the sensor element 1*a* comprising the sensor electrodes 3, 4 is placed on or against the patient P.

The sensor element 1*a* in the present embodiment has an approximately trapezoid basic shape with rounded corners. The total base area of the sensor element 1*a*, measuring 36 cm×24 cm here, is superimposed by an electrode covering 3*a*. The sensor electrodes 3, 4 here have a square basic shape with a side length of 5 cm. The sensor electrodes 3, 4 are placed towards the corners of the sensor element 1*a* at a distance of 4 cm to 5 cm from the edge.

The structure of a signal measuring circuit 30 is explained in greater detail below. Patient P can be provided with a material garment C, for example. The sensor element 1*a* is mechanically stabilized by a supporting structure 22, e.g. a hard shell-like housing of synthetic material with a compressible stabilizing filler material such as a PU foam, for example. Both of the sensor electrodes 3, 4 and the two other sensor electrodes are superimposed by the shared electrode covering 3*a*. The electrode covering 3*a* is designed as an electrically conductive cover layer. The sensor electrodes 3, 4 likewise comprise an electrically conductive layer. The electrode covering 3*a* does not provide complete ohmic insulation of the sensor electrodes 3, 4 from the patient P. In this respect, the electrode covering 3*a* functions as an ohmic resistance which is connected in parallel with the capacitive resistance between patient P and sensor electrode 3, 4. The sensor electrodes 3, 4 can be capacitively coupled to the patient P in any case. With suitable patient clothing and/or a corresponding environmental temperature or environmental (air) humidity, the electrode covering 3*a* and the conductive layer of the sensor electrodes 3, 4 also allow an ohmic connection between patient P and sensor electrodes 3, 4. The capacitive coupling of the ECG signal into the sensor electrodes 3, 4 is not impaired by the sensor covering 3*a*.

This Arrangement Offers the Following Advantages:

As a result of the parallel connection of capacitive and ohmic resistance by means of the electrically conductive electrode covering 3*a*, significantly lower impedances form in comparison with a purely capacitive coupling. This results in an improved ECG signal quality, which is comparable with regular ohmically coupled ECG devices using adhesive electrodes or wrist terminals.

This allows the development of the full characteristic of the classic ECG signal shape including all individual segments and without the suppression of low-frequency components such as the T wave, for example.

Since the electrode covering 3*a* extends over a maximum area of the sensor element 1*a*, an electrostatic discharge (ESD) is possible over the whole area, resulting in lower signal interference.

The shared all-embracing electrode covering 3*a* is easy to manufacture and the structure of the corresponding sensor element 1*a* is likewise simple. The electrode covering 3*a*, particularly when designed as a film of synthetic material, allows a smooth and hygienic surface with good cleaning properties.

If the patient is wearing a textile garment with a bulk resistance of less than 10 GOhm, e.g. a cotton or any other woven material which has been exposed to minimal vapor deposition or sweat, a discharge of electrostatic charges of the patient P occurs via the electrode covering 3*a*, resulting in faster signal initialization.

The sensor electrode 3, a sensor line 6*a* which runs from the sensor electrode 3 to an operational amplifier 27, and the measuring circuit 30 which comprises the operational amplifier 27 are surrounded by a so-called active guard 25 and preferably also a shield S. The operational amplifier 27 is designed as a back-coupled device. This means that the negative input 27*a* of the operational amplifier 27 is coupled to the output 28 of the operational amplifier 27. In this way, a high virtual impedance is achieved at the positive input 27*b* for the operational amplifier 27. This means that as a result of adapting the voltage between the output 28 and the positive input 27*b*, barely any current flows between the sensor 3 and the active guard 25. Furthermore, the positive input 27*b* of the operational amplifier 27 is maintained at an electrical bias voltage with the aid of a resistor 26 which is connected to the measuring device frame (measuring ground). The positive input can therefore be set to a desired measuring potential. It is thereby possible to suppress DC components, in particular during a primarily capacitive coupling.

The signal measuring circuit 30 is also connected to the ground E via a further grounding layer ES.

Shield S is likewise connected to the device frame via connection point 31.

Active guard 25, shield S and grounding layer ES each surround the sensor electrodes 3, 4 in order to provide an effective shield. Active guard 25, shield S and grounding layer ES also surround the sensor line 6*a* and, together with said sensor line 6*a*, pass through the supporting structure 22 on a suitable path to the operational amplifier 27. In particular, active guard 25, shield S and grounding layer ES, as well as the sensor line 6*a* and the operational amplifier 27, are arranged on that side of the sensor electrodes 3, 4 which faces away from the patient P.

A further planar electrode is also provided as a grounding electrode 6 in the sensor element 1*a* shown here, for the purpose of at least capacitive but also ohmic coupling of the patient P to the ground potential E, and is in effect integrated in the sensor element 1*a*. The grounding electrode 6 here has a square basic shape and likewise has a side length of 5 cm. The distance from the sensor electrodes is 4 cm here. Impedance values significantly higher than 200 MOhm can be achieved at this distance.

A further planar electrode, which is designed as a reference electrode 5, together with its associated measuring circuit 36 is used in the sensor element 1*a* for potential discharge, e.g. as a so-called driven neutral electrode (DNE). The reference electrode 5 has a basic shape which is adapted to the arrangement and shape of the other electrodes and essentially occupies all of the regions between the other electrodes, a distance of at least 1 cm from the other electrodes being provided. Impedance values considerably higher than 1 GOhm can be achieved at this distance.

Reference electrode 5 and grounding electrode 6 are likewise spanned by the electrode covering 3*a* and have an electrically conductive layer. By virtue of the coupling of reference electrode 5 and grounding electrode 6 with low impedance, an increase of up to 20 dB is achieved in the suppression of electrical interference fields.

The differential voltage measuring system 1 can optionally comprise a switching apparatus in the form of a switch matrix 33. In the case of multiple sensor electrodes, this is used to select, e.g. as a function of patient anatomy, which of the sensor electrodes will be used for further signal processing.

The differential voltage measuring system 1 can also include a signal processing apparatus in the form of a signal processing box 34. This is designed to undertake preprocessing of the captured measured signals in order to remove interference components. The signal processing apparatus 34 can be designed to execute standard processing using frequency-based filters such as bandpass or bandstop filters, but also an enhanced interference suppression as per the German patent application DE 102019203627A, for example.

The differential voltage measuring system 1 can also comprise a trigger apparatus 35. This is designed to recognize a heartbeat of a patient P or the heartbeat rhythm and to generate control signals therefrom, said control signals comprising trigger information or start-time information for a medical imaging system. On the basis of the control signals from the trigger apparatus 35, the imaging system calculates the time points for an image data capture.

Figure 3:
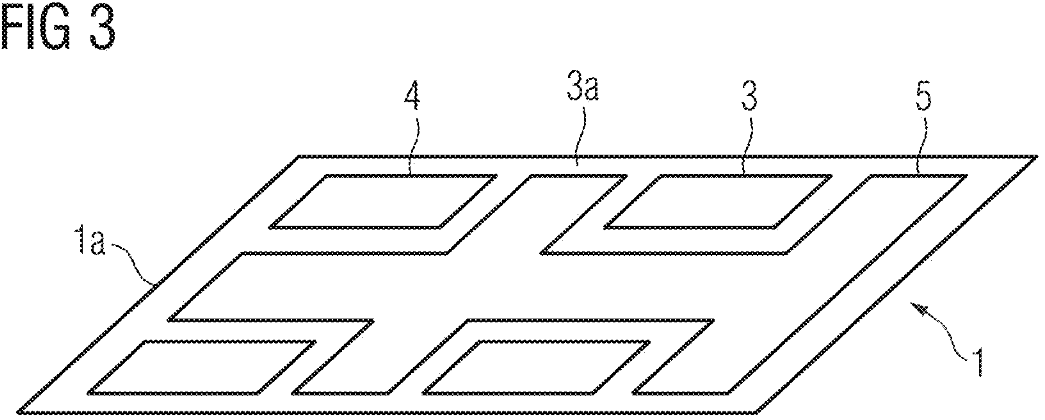
FIG. 3 shows a detail view of a differential voltage measuring system in a further exemplary embodiment.
Figure 4:
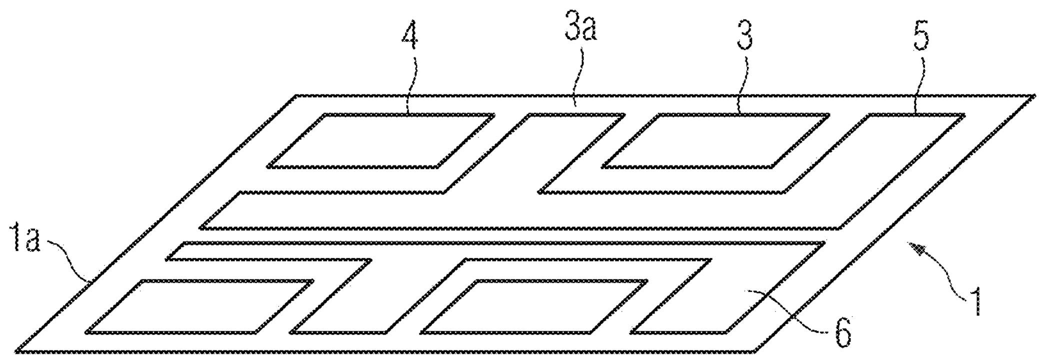
FIG. 4 shows a further detail view of a differential voltage measuring system in an exemplary embodiment.

FIG. 3 and FIG. 4 each show detail views of differential voltage measuring systems 1 according to the present invention in further exemplary embodiments, the layer-type structure of a sensor element 1*a* according to example embodiments of the present invention being shown in particular.

An inventive integrated differential voltage measuring system 1 comprises at least two sensor electrodes 3, 4, each of which belongs to a signal measuring circuit 30. The voltage measuring system here comprises two further sensor electrodes, which can optionally be used to pick up an ECG signal.

The voltage measuring system 1 in FIG. 3 and FIG. 4 also comprises an integral reference electrode 5, which belongs to a corresponding reference measuring circuit.

In FIG. 4, the voltage measuring system 1 also has an integrated grounding electrode 6 belonging to a corresponding grounding circuit. In FIG. 3, the voltage measuring system comprises a grounding electrode which is provided on a further, separate sensor element.

Both the sensor electrodes 3, 4 and the reference electrode 5, and in FIG. 4 also the grounding electrode 6, are inventively superimposed by a shared electrically conductive electrode covering 3*a*, wherein the electrically conductive electrode covering 3*a* spans at least a region that is formed by the base areas of the sensor electrodes and reference electrode. The electrode covering 3*a* here is even somewhat larger, covering the area formed by the base area of the sensor element, and therefore extends beyond sensor electrodes and reference electrode.

The reference electrode 5, the grounding electrode 6 and the sensor electrodes 3, 4 (and the further sensor electrodes) are designed as flat planar layer electrodes arranged on the same plane on that side of the sensor element 1*a* which faces towards the patient P. The height of the various electrodes can range from 300 μm to 3 mm. The electrodes here are intended to have a thickness of 500 μm. The thinner the electrodes, the thinner the corresponding sensor element likewise. Furthermore, the moldability of the electrodes to the anatomy of the patient P can be optimized in the case of thinner layouts. The sensor electrodes here are square, the reference electrode 5 and the grounding electrode 6 being arranged substantially between the sensor electrodes and partially adjacent to each other, but also extending partly beyond the area spanned by the sensor electrodes. In this case, the reference electrode 5 is so shaped as to surround the sensor electrodes over an angular range of at least 180° in each case, i.e. on at least two sides in the case of the square base area here. In alternative embodiments, the reference electrode can also fully enclose the sensor electrodes.

The sensor electrodes, the reference electrode 5 and the grounding electrode 6 have a layer-type structure. They therefore consist of at least two layers. Each of the electrodes comprises at least one upper electrically conductive layer, which can establish an ohmic connection to the patient P via the electrically conductive electrode covering 3*a* in parallel with a capacitive coupling, this having a positive effect on the ECG signal quality as described above.

The electrically conductive electrode covering 3*a* has a layer thickness of 80 μm to 90 80 μm in the embodiments according to FIG. 3 and FIG. 4 and is therefore advantageously thin, this having a positive effect on the overall structural height of the sensor element 1*a*.

The electrode covering 3*a* here is made from a synthetic material into which carbon particles are embedded in order to achieve the desired electrical conducting properties. The saturation level is preferably 10 to 30 percent by volume.

The electrode covering 3*a* in this case is inventively so configured as to have a surface resistance of at least 500 MOhm, preferably higher, and a maximum bulk resistance of 100 MOhm, preferably lower. Resistance values in this case are conformant with the specifications of DIN EN 61340-2-3 (VDE 0300-2-3), Elektrostatik—Teil 2-3: Prüfverfahren zur Bestimmung des Widerstandes and des spezifischen Widerstandes von festen Werkstoffen, die zur Vermeidung elektrostatischer Aufladung verwendet werden [Electrostatics—Part 2-3: Test methods for the determination of the electrical resistance and resistivity of solid materials used to avoid electrostatic charge accumulation] (IEC 61340-2-3:2016).

In FIG. 3 and FIG. 4, the electrode covering is made from a hygroscopic material. These materials bind water from the environment into their molecular structure, whereby the electrical conductivity of the electrode covering 3*a* can be positively influenced when capturing signals.

In both FIG. 3 and FIG. 4, the size of the base area of the reference electrode 5 corresponds to a multiple of the base area of a sensor electrode 3, 4. The reference electrode and in FIG. 4 also the grounding electrode 6 essentially fill in the area of the sensor element 1*a* over which the sensor electrodes extend. It is thereby advantageously possible to achieve a potential equalization over large regions of the sensor element 1*a*, resulting in a high signal quality.

When arranging/distributing the various electrodes over the base area of the sensor element 1*a*, it is important to allow for distances at which sufficiently high impedance values are achieved between the individual electrodes.

A distance must therefore be observed, between the reference electrode 5 and each of the sensor electrodes, which achieves an impedance of at least 100 MOhm between reference electrode and sensor electrode.

With reference to FIG. 4, between the grounding electrode 6 and each of the sensor electrodes a distance must be observed which achieves the impedance of at least 1 GOhm between grounding electrode 6 and sensor electrode, and between the grounding electrode 6 and the reference electrode 5 a distance must be observed which achieves an impedance of at least 200 MOhm between grounding electrode 6 and reference electrode 5.

In conclusion, it is again noted that the apparatuses described in detail above are merely exemplary embodiments which can be modified in all manner of ways by a person skilled in the art without thereby departing from the scope of the present invention. For example, the differential voltage measuring system need not be an ECG device, but could also be other medical devices which are used to capture bioelectrical signals, such as, for example, EEGs, EMGs, etc. Furthermore, use of the indefinite article "a" or "an" does not preclude multiple instances of the features concerned.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term ‘module’, ‘interface’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where not explicitly developed but nonetheless beneficial and in accordance with the present invention, individual exemplary embodiments as well as individual partial aspects or features thereof can be combined or substituted without thereby departing from the scope of the present invention. Advantages of the present invention which are described with reference to one exemplary embodiment also apply without being named explicitly to other exemplary embodiments where transferable.

The invention claimed is:

1. An integrated differential voltage measuring system for measuring bioelectrical signals of a patient, the integrated differential voltage measuring system comprising:

at least two signal measuring circuits, each of the at least two signal measuring circuits including, a sensor electrode;

a reference measuring circuit comprising a reference electrode; and a shared electrically conductive electrode covering having a surface resistance which is greater than 500 MOhm, the electrically conductive electrode covering configured to be placed between the sensor electrode and a garment worn by the patient and between the reference electrode and the garment worn by the patient, and to create an ohmic resistance between the patient and the sensor electrode via the shared electrically conductive electrode covering, wherein the electrically conductive electrode covering superimposes at least a region that is formed by base areas of the sensor electrode and the reference electrode.

2. The differential voltage measuring system as claimed in claim 1, wherein the electrically conductive electrode covering is made from a synthetic material.

3. The differential voltage measuring system as claimed in claim 1, wherein the base area of the reference electrode corresponds to a multiple of the base area of one of the sensor electrodes.

4. The differential voltage measuring system as claimed in claim 1, wherein the reference electrode surrounds each sensor electrode over an angular range of at least 180°.

5. The differential voltage measuring system as claimed in claim 1, wherein an impedance between the reference electrode and each sensor electrode is greater than 100 MOhm in each case.

6. The differential voltage measuring system as claimed in claim 1, wherein the shared electrically conductive electrode covering is electrically connected to the sensor electrodes.

7. The differential voltage measuring system as claimed in claim 1, wherein the shared electrically conductive electrode covering is made from a hygroscopic material.

8. The differential voltage measuring system as claimed in claim 1, wherein the electrically conductive electrode covering is enriched with carbon particles.

9. The differential voltage measuring system as claimed in claim 8, wherein the electrically conductive electrode covering has a bulk resistance of less than 100 MOhm.

10. The differential voltage measuring system as claimed in claim 1, further comprising:

a grounding circuit including a grounding electrode, wherein a base area of the grounding electrode is superimposed by the electrically conductive electrode covering.

11. The differential voltage measuring system as claimed in claim 10, wherein an impedance between the grounding electrode and each sensor electrode is greater than 1 GOhm, and an impedance between the grounding electrode and the reference electrode is greater than 200 MOhm.

12. The differential voltage measuring system as claimed in claim 1, wherein the sensor electrode and the reference electrode have a layer-type structure, each of the sensor electrode and the reference electrode including at least one upper electrically conductive layer.

13. The differential voltage measuring system as claimed in claim 12, wherein the electrically conductive electrode covering has a layer thickness of less than 100 μm.

14. The differential voltage measuring system as claimed in claim 12, wherein the electrically conductive electrode covering is made from a synthetic material.

15. The differential voltage measuring system as claimed in claim 1, wherein the electrically conductive electrode covering has a layer thickness of less than 100 μm.

16. The differential voltage measuring system as claimed in claim 15, wherein the electrically conductive electrode covering is made from a synthetic material.

17. An integrated differential voltage measuring system for measuring bioelectrical signals of a patient, the integrated differential voltage measuring system comprising:

at least two signal measuring circuits, each of the at least two signal measuring circuits including, a sensor electrode;

a reference measuring circuit comprising a reference electrode; and a shared electrically conductive electrode covering configured to be placed between the sensor electrode and the patient and between the reference electrode and the patient, wherein the electrically conductive electrode covering superimposes at least a region that is formed by base areas of the sensor electrode and the reference electrode, wherein the electrically conductive electrode covering has a surface resistance which is greater than 500 MOhm, and wherein the electrically conductive electrode covering has a bulk resistance of less than 100 MOhm.

18. The integrated differential voltage measuring system as claimed in claim 17, wherein the electrically conductive electrode covering is enriched with carbon particles.

19. An integrated differential voltage measuring system, on a garment, for measuring bioelectrical signals of a patient, the integrated differential voltage measuring system comprising:

at least two measuring circuits, each of the at least two measuring circuits including, a sensor electrode;

a reference measuring circuit comprising a reference electrode; and a shared electrically conductive electrode covering having a surface resistance which is greater than 500 MOhm, the shared electrically conductive electrode covering comprising a conductive material, configured to be placed between the sensor electrode and the garment worn by the patient and between the reference electrode and the garment worn by the patient, wherein the electrically conductive electrode covering superimposes at least a region that is formed by base areas of the sensor electrode and the reference electrode, and wherein the garment and the shared electrically conductive electrode covering are configured to create an ohmic resistance which is connected in parallel with a capacitive resistance between the patient and the sensor electrode.

* * * * *